(12) United States Patent
Zhu et al.

(10) Patent No.: US 12,171,856 B2
(45) Date of Patent: Dec. 24, 2024

(54) USE OF SALIDROSIDE DERIVATIVE IN EXTERNAL PREPARATION FOR SKIN WHITENING

(71) Applicant: SHANGHAI CHEERMORE BIOLOGICAL TECHNOLOGY CO., LTD, Shanghai (CN)

(72) Inventors: Caibin Zhu, Shanghai (CN); Junxiang Li, Shanghai (CN)

(73) Assignee: SHANGHAI CHEERMORE BIOLOGICAL TECHNOLOGY CO., LTD, Shanghai (CN)

( * ) Notice: Subject to any disclaimer, the term of this patent is extended or adjusted under 35 U.S.C. 154(b) by 746 days.

(21) Appl. No.: 17/432,492

(22) PCT Filed: Nov. 18, 2020

(86) PCT No.: PCT/CN2020/129731
§ 371 (c)(1),
(2) Date: Aug. 20, 2021

(87) PCT Pub. No.: WO2021/129241
PCT Pub. Date: Jul. 1, 2021

(65) Prior Publication Data
US 2022/0142895 A1 May 12, 2022

(30) Foreign Application Priority Data
Dec. 26, 2019 (CN) .................. 201911367032.4

(51) Int. Cl.
*A61K 8/60* (2006.01)
*A61Q 19/02* (2006.01)

(52) U.S. Cl.
CPC .............. *A61K 8/602* (2013.01); *A61Q 19/02* (2013.01)

(58) Field of Classification Search
CPC ................................ A61K 8/602; A61Q 19/02
See application file for complete search history.

(56) References Cited

FOREIGN PATENT DOCUMENTS

| CN | 1475492 A | 2/2004 |
|----|-----------|--------|
| CN | 1520804 A | 8/2004 |
| CN | 102641233 A | 8/2012 |
| CN | 104606067 A | 5/2015 |
| CN | 108420770 A | 8/2018 |
| CN | 108524337 A | 9/2018 |
| CN | 109939052 A | 6/2019 |
| CN | 110964066 A | 4/2020 |

OTHER PUBLICATIONS

CN 1475492 A machine translation google patent (Year: 2004).*
CN 104606067 A machine translation google patent (Year: 2015).*
Chang Li, Synthesis, Characterization and Study on Whitening Activity of Glucoside-phenols Conjugates, 2017, pp. 1-60.
Yu-Ming Pu, et al., An Expedient and Multikilogram Synthesis of a Naphthalenoid H3 Antagonist, Organic Process Research & Development, 2007, pp. 1004-1009, 11.

* cited by examiner

*Primary Examiner* — Robert A Wax
*Assistant Examiner* — William Craigo
(74) *Attorney, Agent, or Firm* — Bayramoglu Law Offices LLC (57) ABSTRACT

The use of the compound or a pharmaceutically acceptable salt thereof in the preparation of an external preparation for skin whitening is provided, and the compound is shown in formula (I-1):

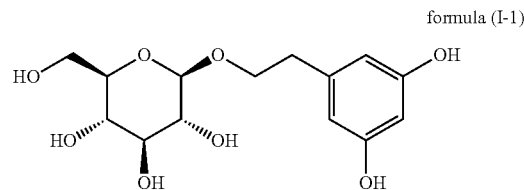

formula (I-1)

The present disclosure can enhance the whitening activity of salidroside while taking full advantage of the protective effect of salidroside sugar ring, where the phenol residues of salidroside are restructured to obtain salidroside-plus (SP-037), which is 1-(3,5-dihydroxyphenyl)ethyl-β-D-glucoside and/or a salt thereof. The whitening effect of the compound is tested through a series of experiments.

7 Claims, 7 Drawing Sheets

USE OF SALIDROSIDE DERIVATIVE IN EXTERNAL PREPARATION FOR SKIN WHITENING

CROSS REFERENCE TO THE RELATED APPLICATIONS

This application is the national phase entry of International Application No. PCT/CN2020/129731, filed on Nov. 18, 2020, which is based upon and claims priority to Chinese Patent Application No. 201911367032.4, filed on Dec. 26, 2019, the entire contents of which are incorporated herein by reference.

TECHNICAL FIELD

The present disclosure belongs to the technical field of skin care products, and specifically relates to the use of a salidroside derivative in an external preparation for skin whitening.

BACKGROUND

The content and distribution of melanin in the skin determine the color of human skin. The generation of melanin is related to tyrosine, tyrosinase, active oxygen, and melanosome. External stimuli such as ultraviolet (UV) radiation can cause the activation of tyrosinase, then tyrosine is oxidized into L-dopa under the action of tyrosinase, and L-dopa is further oxidized into melanin; and melanin is transferred to the skin surface and causes dull skin, local spots, and other phenomena, and finally permanent pigmentation spots are formed due to abnormal skin metabolism. Therefore, skin whitening can be achieved through the following ways: isolating UV rays, scavenging oxygen free radicals (OFRs), inhibiting tyrosinase, blocking melanin transfer, etc. However, excessively inhibiting the melanin synthesis will severely damage existing melanocytes and make melanocytes insufficient, which will cause the skin to become abnormally white and further cause vitiligo. Scientifically inhibiting melanin will not threaten the physical health.

In modern society, it is more and more popular to pursue beauty and the concept of "one white covers up a hundred ugliness" is recognized by more and more people, and many people want to keep the skin white. Therefore, whitening and despeckling products have become a popular choice, and the various types of whitening cosmetics are growing. At present, there are whitening products such as creams, lotions, gels, and facial masks on the market. Among these products, many products will make the skin abnormally white or uncomfortably white, which obviously runs counter to the original intention of whitening. Therefore, there is an urgent need to develop a new ingredient that can accelerate the metabolism of melanocytes without destroying the normal metabolism of skin, such that melanin will not be excessively deposited to form pigmentation spots, thereby achieving healthy skin whitening.

SUMMARY

The present disclosure is intended to provide a salidroside derivative that inhibits the generation of melanin and brightens the skin, a preparation method thereof, and use thereof in a whitening cosmetic.

Salidroside is a sugar ring-containing polyphenolic compound, which has the effects of immunoregulation, anti-hypoxia, and antisenility. Moreover, salidroside is reported to have a specified whitening effect in some literatures. The present disclosure speculates that salidroside plays a whitening role through its phenol residues.

In one aspect, the present disclosure provides a compound of formula (I):

formula (I)

where $R_1$, $R_2$, $R_3$, $R_4$, and $R_5$ are hydrogen atoms or hydroxyl groups; and n is an alkyl group with 1 to 3 carbon atoms.

Further, when n is an alkyl group with 1 carbon atom, $R_1$ is a hydrogen atom, $R_2$ is a hydroxyl group, $R_3$ is a hydrogen atom, $R_4$ is a hydroxyl group, and $R_5$ is a hydrogen atom, the compound has the following name: 1-(3,5-dihydroxyphenyl)ethyl-β-D-glucoside, with a chemical formula of $C_{13}H_{18}O_8$ and a structure shown in formula (I-1):

formula (I-1)

In one aspect, the present disclosure also provides a preparation process of the compound of formula (I-1), including the following steps:

Step 1:

dissolving 3,5-dihydroxyphenylacetic acid and borane-tetrahydrofuran (THF) at a molar ratio of 1:(1.1-1.3) in THF to react at 15° C. to 25° C. for 4 h to 6 h; after the reaction is completed, conducting rotary evaporation for solvent removal to obtain a crude product; and purifying the crude product by column chromatography to obtain an intermediate 2;

Step 2:

dissolving the intermediate 2 obtained in step 1 and benzyl chloride in acetone by stirring, where a molar ratio of the intermediate 2 to the benzyl chloride is 1:(1-1.2) and the stirring is conducted at a rotational speed of 200 rpm to 300 rpm; after the dissolution is completed, adding potassium carbonate and potassium iodide to react at reflux for 18 h to 20 h, where a molar ratio of the intermediate 2 to the potassium carbonate is 1:(1-1.2) and a molar ratio of the intermediate 2 to the potassium iodide is 1:(0.1-0.2); evaporating the solvent, pouring a residue into water, and adding hydrochloric acid dropwise to adjust a pH to 7; conducting extraction with ethyl acetate, evaporating the solvent out from a resulting organic phase under vacuum, and subjecting a resulting product to recrystallization with absolute ethanol to obtain a white solid intermediate 3;

Step 3:

dissolving the intermediate 3 obtained in step 2 in dichloromethane (DCM), and adding an intermediate 4, a molecular sieve, and dry silver carbonate sequentially under stirring to react at 15° C. to 25° C. for 24 h to 36 h in the dark, where a molar ratio of the intermediate 3 to the intermediate 4 is 1:(1.2-1.4), the molecular sieve is added at an amount of 2 g to 3 g, a molar ratio of the intermediate 3 to the dry silver carbonate is 1:(0.6-0.7), and the stirring is conducted at a rotational speed of 200 rpm to 300 rpm; after the reaction is completed, filtering a resulting mixture to obtain a filter cake and a filtrate; and washing the filter cake with DCM, and concentrating the filtrate to obtain an intermediate 5;

Step 4:

dissolving the intermediate 5 obtained in step 3 in absolute methanol, adding sodium methoxide, and stirring for 6 h to 8 h at a temperature of 15° C. to 25° C. and a rotational speed of 200 rpm to 300 rpm; adjusting a pH to 6 with acetic acid, filtering a resulting mixture to obtain a filtrate, and concentrating the filtrate under vacuum to obtain a viscous material; adding methanol and palladium carbon to the viscous material, and stirring to react for 4 h to 6 h under hydrogen pressurization; and purifying a reaction product by column chromatography to obtain a final product 6 with a structure shown in formula (I-1).

In another aspect, the present disclosure also provides use of the compound of formula (I) or a pharmaceutically acceptable salt thereof in the preparation of an external preparation for skin whitening.

Further, the external preparation may be an antioxidant, a colorant, a depigmenting agent, an emollient, an emulsifier, an exfoliant, a fragrance, a humectant, a lubricant, a pharmaceutically active agent, a humidizer, a light fasting agent, a preservative, a skin protectant, a skin penetration enhancer, a sunscreen, a stabilizer, a surfactant, a thickener, or a cosmetic.

Further, the skin protectant may be toner, lotion, cream, essence, and facial mask.

Further, the compound or the pharmaceutically acceptable salt thereof may have a mass percentage of 0.5% to 30% in the external preparation for skin whitening.

Specifically, the compound of formula (I) or the pharmaceutically acceptable salt thereof may be present in the form of an aqueous lotion, a water-in-oil or oil-in-water emulsion, an oil or oleyl alcohol lotion, or a gel.

The present disclosure has the following advantages:

The present disclosure enhances the whitening activity of salidroside while taking full advantage of the protective effect of salidroside sugar ring, where the phenol residues of salidroside are restructured to obtain salidroside-plus (SP-037), which is 1-(3,5-dihydroxyphenyl)ethyl-β-D-glucoside and/or a salt thereof. The whitening effect of the compound is tested through a series of experiments.

BRIEF DESCRIPTION OF THE DRAWINGS

For those of ordinary skill in the art, other relevant drawings can be derived based on the above drawings without creative efforts.

DETAILED DESCRIPTION OF THE EMBODIMENTS

In order to make the present disclosure more comprehensible for those skilled in the art, the technical solutions of the present disclosure are further described below with reference to specific examples.

Example 1: Preparation of 1-(3,5-dihydroxyphenyl)ethyl-β-D-glucoside

Step 1:

1.18 g of 3,5-dihydroxyphenylacetic acid and 8.4 ml of BH3.THF (1.0 M in THF) were dissolved in 20 ml of THF to react at room temperature for 4 h; after the reaction was completed, the solvent was removed by rotary evaporation to obtain a crude product; and the crude product was purified by column chromatography to obtain 1.05 g of a product, with a yield of 97.%

Step 2:

2

3

16.9 g of the intermediate 2, 6.9 mL of benzyl chloride, and 200 mL of acetone were added to a reaction flask sequentially, and a resulting mixture was stirred for dissolution; 8.3 g of potassium carbonate and 0.8 g of potassium iodide were added to react at reflux for 18 h, during which the reaction at reflux was monitored by TLC; the solvent was evaporated, the residue was poured into 200 mL of water, and hydrochloric acid was added dropwise to adjust a pH to 7; and extraction was conducted with ethyl acetate, the solvent was evaporated out from a resulting organic phase under vacuum, and a resulting product was subjected to recrystallization with absolute ethanol to obtain 210.7 g of a white solid, with a recovery rate of 88.6%.

Step 3:

5

27.3 g of the white solid obtained in step 2 was dissolved in 200 mL of CH$_2$Cl$_2$, and 14.8 g of an intermediate 4, 2 g of a molecular sieve, and 55 g of dry silver carbonate were added under stirring to react for 1 day at room temperature in the dark; a resulting mixture was filtered to obtain a filter cake and a filtrate; and the filter cake was washed with an appropriate amount of CH$_2$Cl$_2$ and the filtrate was concentrated to obtain and intermediate 5.

Step 4:

The intermediate 5 obtained in step 3 was dissolved in 150 mL of absolute methanol, 1.6 g of sodium methoxide was added, and a resulting mixture was stirred at room temperature for 6 h; a pH was adjusted to 6 with acetic acid, a resulting mixture was filtered to obtain a filtrate, and the filtrate was concentrated under vacuum to obtain a viscous material; 150 ml of methanol and 0.16 g of palladium carbon were added to the viscous material, and a resulting mixture was stirred to react for 4 h under hydrogen pressurization; and a reaction product was purified by column chromatography to obtain 5.6 g of a final product.

Figure 2:
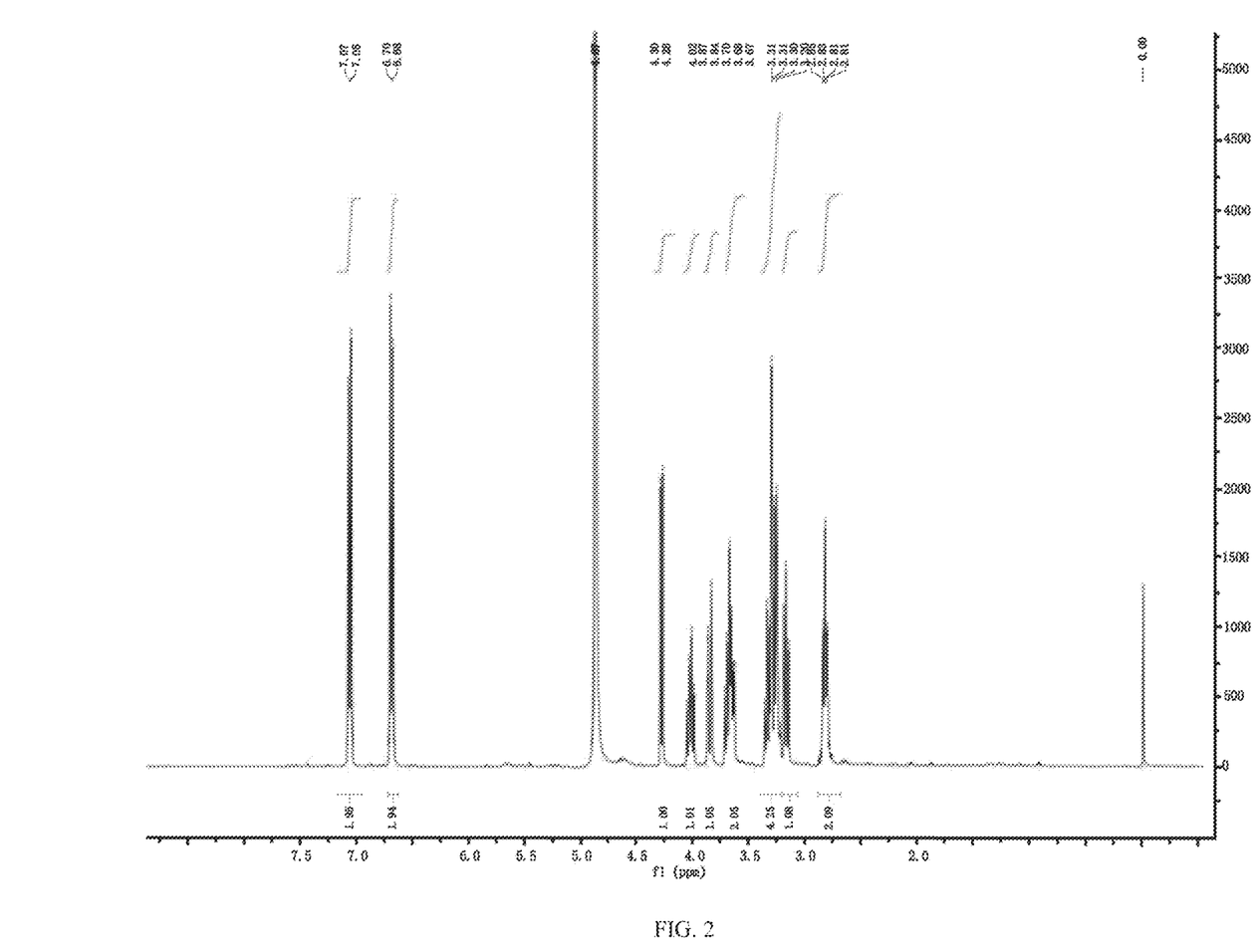
FIG. 2 is an H$^1$-NMR spectrum of 1-(3,5-dihydroxyphenyl)ethyl-β-D-glucoside prepared in Example 1.

Characterization Data:

As shown in FIG. 2, H$^1$-NMR (CD3OD, 400 MHz) δ: 7.06 (2H, d, J=8.4 Hz), 6.69 (2H, d, J=8.4 Hz,), 4.29 (1H, d, J=8.0 Hz), 4.02 (1H, m), 3.86 (1H, dd, J=1.6, 12.4 Hz), 3.68 (2H, overlapped), 3.23-3.37 (3H, overlapped), 3.18 (1H, t, J=8.8 Hz), 2.83 (2H, t, J=8.0 Hz).

Figure 3:
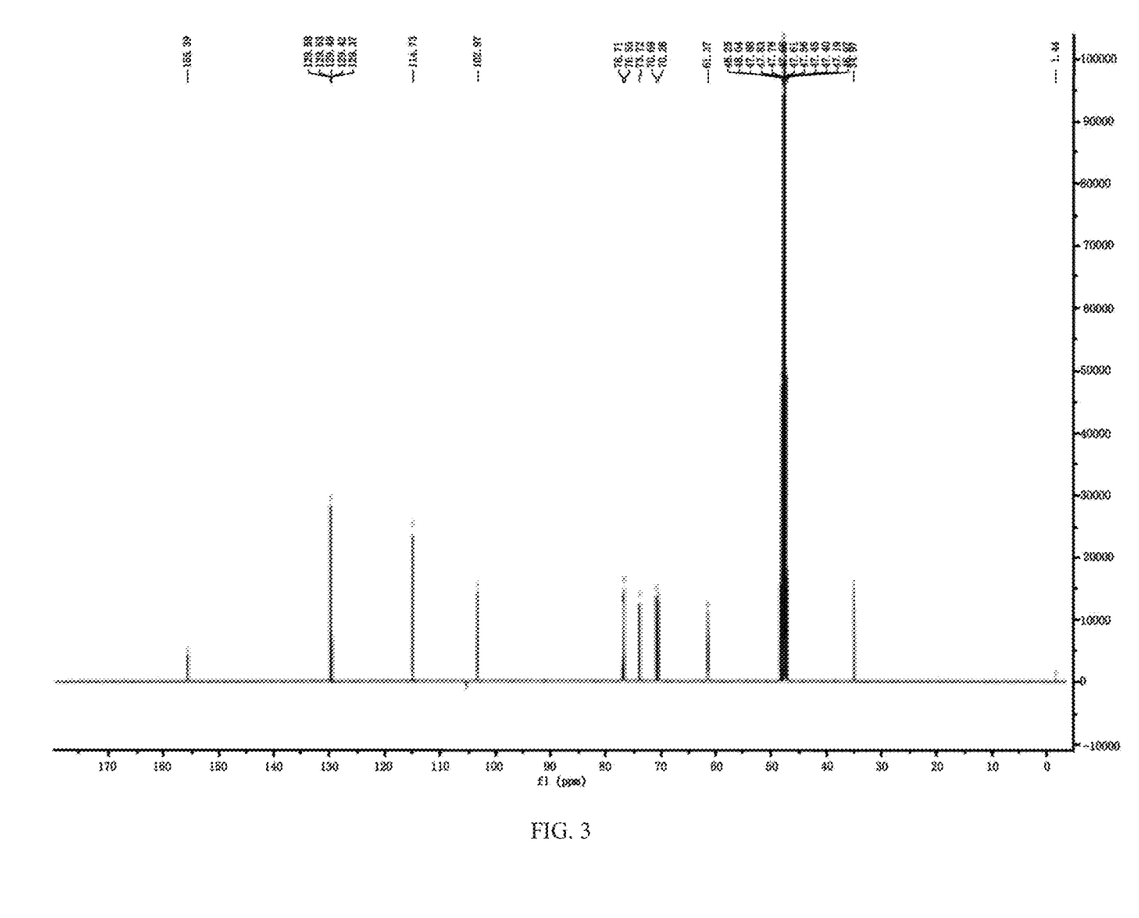
FIG. 3 is a C$^{13}$-NMR spectrum of 1-(3,5-dihydroxyphenyl)ethyl-β-D-glucoside prepared in Example 1.

As shown in FIG. 3, C$^{13}$-NMR (CD3OD, 100 MHz) δ: 155.4, 129.6, 129.4, 114.7, 103.0, 76.7, 76.6, 73.7, 70.7, 70.3, 61.4, 35.0.

Figure 4:
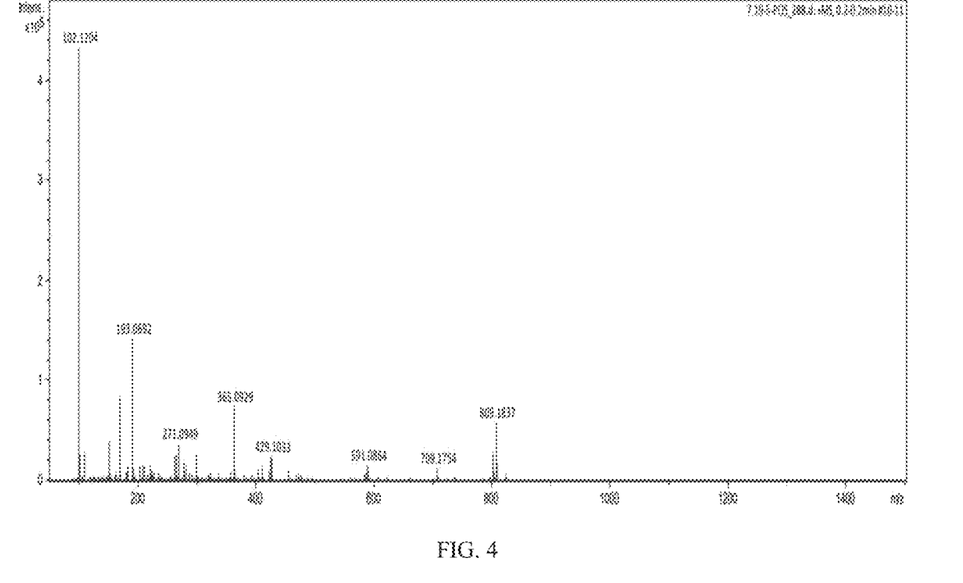
FIG. 4 is an MS spectrum of 1-(3,5-dihydroxyphenyl)ethyl-β-D-glucoside prepared in Example 1.

As shown in FIG. 4, HRESI-MS m/z [M+Na]+: 365.0929.

Example 2: Detection of the Effects of β-D-Glucoside Derivatives on a Simulated Melanin Synthesis Process of In Vitro Melanocytes a. Detection of the Activity of β-D-Glucoside Derivatives to Inhibit the Generation of Melanin

Detection Method:

Human melanocytes and tool melanocytes were used to conduct the experiment in this section. Human melanocytes and tool melanocytes were inoculated in a 96-well plate, with a plating density of 5,000 cells/well. After the cells adhered to a wall, nerve growth factor (NGF) was added to the culture and the culture was irradiated with UV to induce the generation of melanin, which simulated a melanin generation process in vivo. Then β-D-glucoside derivatives to be tested each were added at a final concentration of 100 μM to the cells, and the cells were further cultivated in an incubator at 37° C. and 5% $CO_2$ for 60 h, where 3 replicates were set for each group. The cells were washed with pre-cooled phosphate buffered saline (PBS), then digested with trypsin, and centrifuged, and a resulting supernatant was discarded. The cells were lysed with a NaOH (1 mol/L) solution including 10% dimethyl sulfoxide (DMSO) in a 65° C. water bath to make melanin granules completely dissolved out, and the absorbance at 490 nm was determined with a microplate reader. Finally, the absorbance value was used to reflect a melanin content.

Results and Discussion:

The β-D-glucoside derivatives to be tested in the experiment are selected from compounds with the following chemical formula:

formula (I)

where $R_1$, $R_2$, $R_3$, $R_4$, and $R_5$ are hydrogen atoms or hydroxyl groups, including 1 to 5 hydroxyl groups; and n represents an alkyl group with 1 to 3 carbon atoms. There are 39 β-D-glucoside derivatives of SP-001 to SP-039 in total, with chemical formulas shown as follows:

SP-001

SP-002

SP-003

SP-004

SP-005

SP-006

SP-007

SP-008

SP-009

SP-010

-continued

SP-011

SP-012

SP-013

SP-014

SP-015

SP-016

SP-017

SP-018

-continued

SP-019

SP-020

SP-021

SP-022

SP-023

SP-024

SP-025

SP-026

-continued

SP-027

SP-028

SP-029

SP-030

SP-031

SP-032

SP-033

SP-034

-continued

SP-035

SP-036

SP-037

SP-038

SP-039

Figure 1:
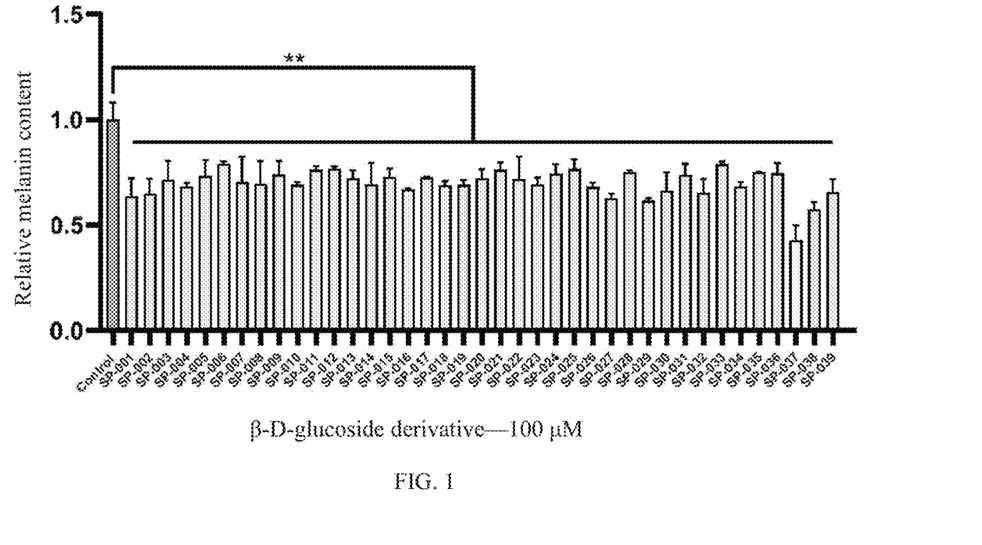
FIG. 1 shows the effects of β-D-glucoside derivatives on a melanin content (mean±SD; n=3; **P<0.01).

As shown in FIG. 1, the 39 β-D-glucoside derivatives to be tested can significantly inhibit the generation of melanin at a cellular level, where the 1-(3,5-dihydroxyphenyl)ethyl-β-D-glucoside numbered SP-037 shows the optimal effect. SP-037 is used for reference to 1-(3,5-dihydroxyphenyl)ethyl-β-D-glucoside hereinafter.

b. Detection of the Activity of SP-037 to Inhibit the Generation of Melanin

Detection Method:

Human melanocytes and tool melanocytes were used to conduct the experiment in this section. Human melanocytes and tool melanocytes were inoculated in a 96-well plate, with a plating density of 5,000 cells/well. After the cells adhered to a wall, NGF was added to the culture and the culture was irradiated with UV to induce the generation of melanin, which simulated a melanin generation process in vivo. SP-037 was added to the cells at 6 concentrations of 0 μM, 12.5 μM, 25 μM, 50 μM, 100 μM, and 200 μM, and then the cells were further cultivated in an incubator at 37° C. and 5% $CO_2$ for 60 h, where 5 replicates were set for each group. The cells were washed with pre-cooled PBS, then digested with trypsin, and centrifuged, and a resulting supernatant was discarded. The cells were lysed with a NaOH (1 mol/L) solution including 10% DMSO in a 65° C. water bath to make melanin granules completely dissolved out, and the absorbance at 490 nm was determined with a microplate reader. Finally, the absorbance value was used to reflect a melanin content.

Figure 5:
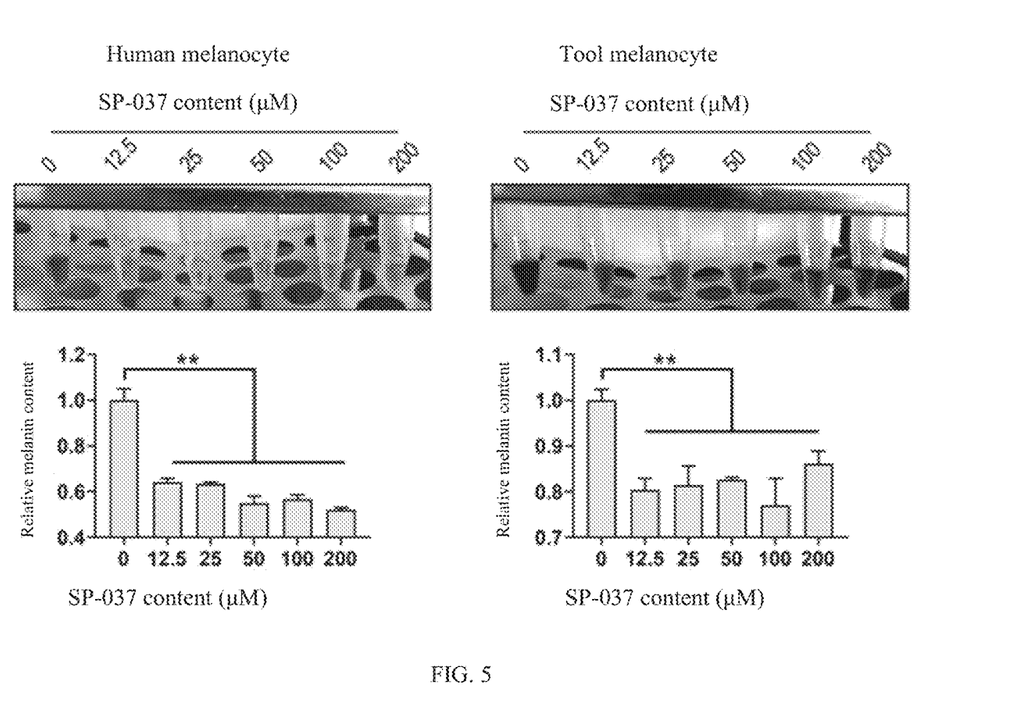
FIG. 5 shows the effect of SP-037 on a melanin content (mean±SD; n=5; **P<0.01).

Results and Discussion:

As shown in FIG. 5, SP-037 can significantly inhibit the generation of melanin at a cellular level, showing an ideal effect at the concentration of 50 μM. This concentration will be used for subsequent experiments.

c. Melanin Inhibition Effect Comparison Between SP-037 and Whitening Positive Drugs Detection Method:

Human melanocytes and tool melanocytes were used to conduct the experiment in this section. Human melanocytes and tool melanocytes were inoculated in a 96-well plate, with a plating density of 5,000 cells/well. After the cells adhered to a wall, NGF was added to the culture and the culture was irradiated with UV to induce the generation of melanin, which simulated a melanin generation process in vivo. 5 drugs of control, SP-037, VC, kojic acid, and hydroquinone were added, separately, and then the cells were further cultivated in an incubator at 37° C. and 5% $CO_2$ for 60 h, where 5 replicates were set for each group. The cells were washed with pre-cooled PBS, then digested with trypsin, and centrifuged, and a resulting supernatant was discarded. The cells were lysed with a NaOH (1 mol/L) solution including 10% DMSO in a 65° C. water bath to make melanin granules completely dissolved out, and the absorbance at 490 nm was determined with a microplate reader. Finally, the absorbance value was used to reflect a melanin content.

Figure 6:
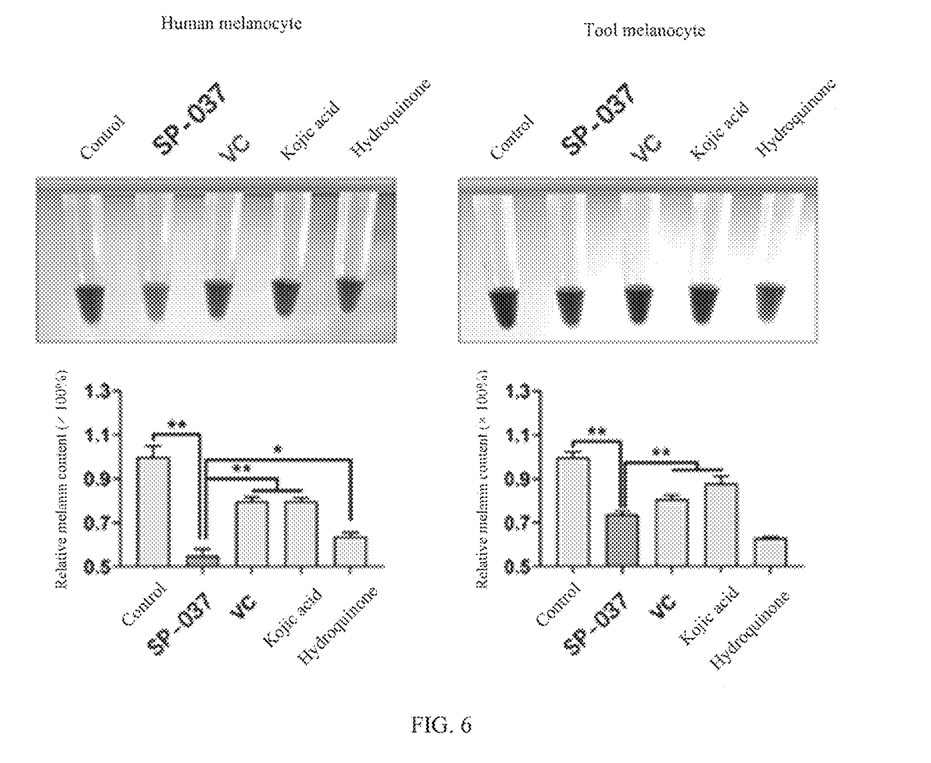
FIG. 6 shows the melanin inhibition effect comparison between SP-037 and whitening positive drugs (mean±SD; n=5; **P<0.01).

Results and Discussion:

As shown in FIG. 6, in human melanocytes, the inhibitory activity of SP-037 on the in vitro simulated melanin generation process is significantly better than that of the positive drugs VC, kojic acid, and hydroquinone. In tool melanocytes, the inhibitory activity of SP-037 on melanin generation is significantly better than that of VC and kojic acid, but slightly inferior to that of hydroquinone.

Example 3: SP-037 Safety Evaluation a. Long-Term Toxicity Test on Mouse Skin

Test Method:

Kunming mice were used to conduct the experiment in this section. SP-037 was prepared into solutions with concentrations of 2.5% (mass to volume ratio), 5% (mass to volume ratio), and 10% (mass to volume ratio) using NS. A control group, a 2.5% dosage group, a 5% dosage group, and a 10% dosage group were set, separately. One mouse was used for the blank group, and two mice were used for each of the experimental groups. Application on the dorsal skin: the hair on the back of mice was removed by depilatory cream, and a drug was applied at a corresponding concentration on the bare skin every day, which lasted for 3 months. During the test period, pictures were taken and the body weight of mice were recorded regularly, and it was observed whether there were white spots and other skin irritation or poisoning phenomena.

Figure 7:
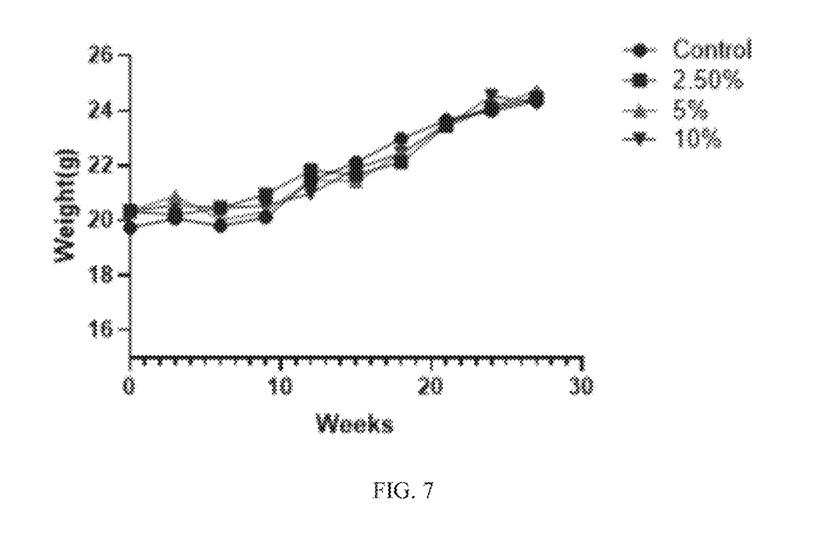
FIG. 7 shows the body weight change of mice (Control: a group applied with normal saline (NS); 2.5%: a group applied with NS including 2.5% SP-037; 5%: a group applied with NS including 5% SP-037; and 10%: a group applied with NS including 10% SP-037).
Figure 8:
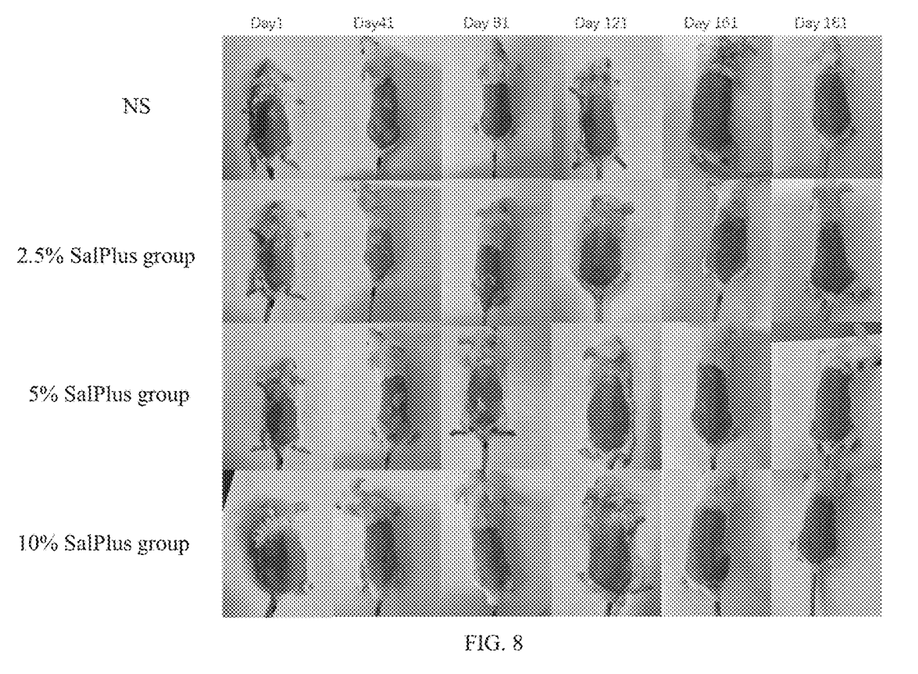
FIG. 8 shows the skin monitoring results of mice (Control: a group applied with NS; 2.5%: a group applied with NS including 2.5% SP-037; 5%: a group applied with NS including 5% SP-037; and 10%: a group applied with NS including 10% SP-037).

Results and Discussion:

As shown in FIG. 7 and FIG. 8, during the period where the mice used for the long-term toxicity test were applied with SP-037 at a specified concentration consecutively for 6 months, the changes in the body weight and skin condition are in line with the growth pattern of normal mice, and none of the mice has white spots, redness and swelling, and other skin irritation injuries, or poisoning symptoms such as convulsion, tail erection, kicking, flipping, and death. The long-term toxicity test shows that SP-037 will not cause white spots, skin irritation, and toxicity at a dosage of 10% (mass to volume ratio).

b. Human Skin Irritation Test

In order to further achieve the use of SP-037 in the field of skin care, it is necessary to ensure the safety of SP-037 first. In the experiment of this section, a gel (2% sodium carboxymethyl cellulose prepared with deionized water) with the main component of 10% SP-037 was prepared, then volunteers were recruited, and a patch test was conducted on the arm skin of the volunteers to evaluate the safety of SP-037.

Figure 9:
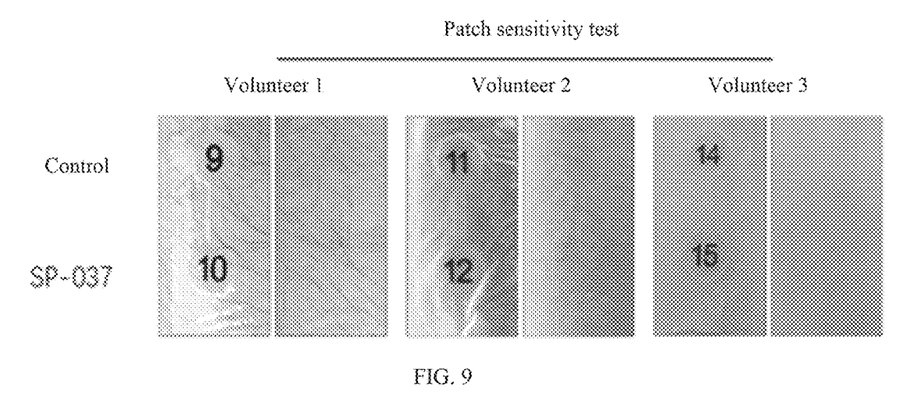
FIG. 9 shows patch sensitivity test results of SP-037.

Results and Discussion:

As shown in FIG. 9, results of the patch test show that SP-037 has no sensitization to the skin, and the volunteers feel no irritating pain, itching, or the like during the test, indicating that SP-037 has high safety.

Example 4: Detection of the Skin Whitening Effect of SP-037

Detection Method:

A total of 33 volunteers with dark skin were recruited, and the 33 volunteers were 22 to 38 years old. The 33 volunteers were randomly divided into 7 groups, including: a blank control group: 3, an SP-037 group: 5; a VC group: 5; a kojic acid group: 5; a thiamidol group: 5; a hydroquinone group: 5; and a 377 group: 5. A blank gel and gels with the main components of SP-037, VC, kojic acid, thiamidol, hydroquinone, and 377 respectively were prepared. An inner side of the left arm of each volunteer in each group was washed and then evenly applied with a corresponding gel every day, which lasted for 4 weeks. The Dermalab instrument was used to determine the characteristics of skin at the inner side of the arm with a skin color test probe on day 0, day 14, and day 28 to obtain melanin and L*a*b values, and according to final statistical data, the whitening effect of each component was analyzed.

Figure 10:
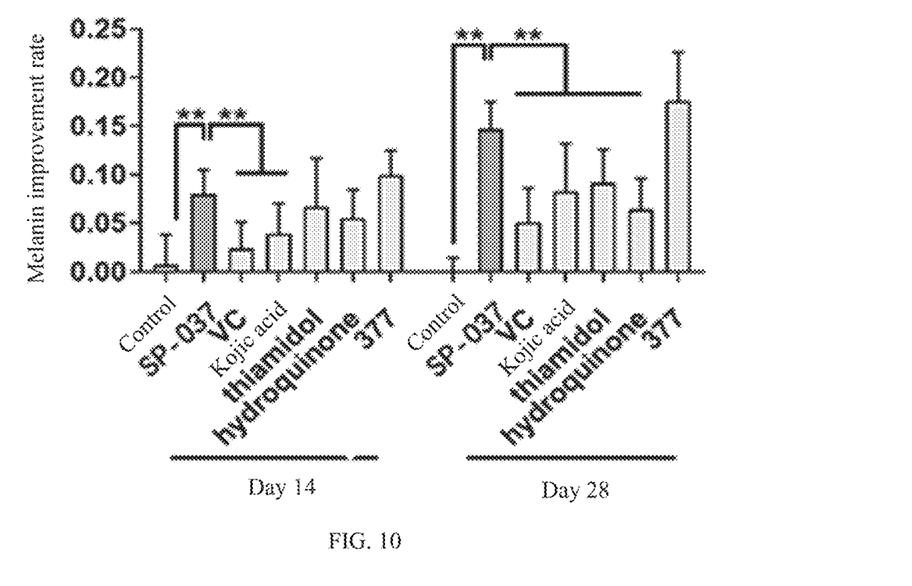
FIG. 10 shows the effect of SP-037 on a melanin content in skin (mean±SD; **P<0.01).
Figure 11:
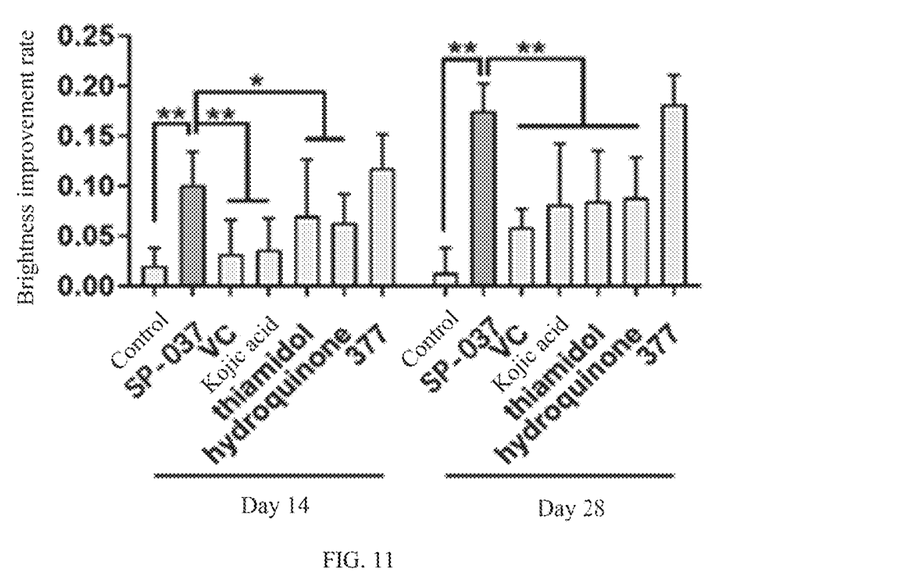
FIG. 11 shows the effect of SP-037 on skin brightness (mean±SD; *P<0.05, **P<0.01).

Results and Discussion:

As shown in FIG. 10 and FIG. 11, results of the skin test show that SP-037 can significantly improve the skin melanin pigmentation and improve the skin brightness. The effect of SP-037 is significantly better than that of raw materials VC, kojic acid, thiamidol, and hydroquinone currently on the market, but slightly inferior to that of 377 (phenylethyl resorcinol). SP-037 has high safety and no sensitization or irritation. At a cellular level, SP-037 can effectively inhibit the generation of inducible melanin; and the results of the further volunteer experiment show that SP-037 is ideal for improving skin melanin pigmentation and increasing skin brightness.

The present disclosure is exemplarily described above. It should be noted that, without departing from the core of the present disclosure, any simple variation, modification, or equivalent substitutions made by those skilled in the art without creative efforts shall fall within the protection scope of the present disclosure.

What is claimed is:

1. A method of whitening skin with a skin whitening compound or a pharmaceutically acceptable salt of the skin whitening compound, the skin whitening compound consists of formula (I-1):

formula (I-1)

the method comprising:
applying the skin whitening compound or the pharmaceutically acceptable salt of the skin whitening compound to skin of a human subject, and
inhibiting melanocyte production of melanin in the skin with the applied skin whitening compound or pharmaceutically acceptable salt of the skin whitening compound to thereby whitening the skin by reducing melanin content in the skin.

2. The method according to claim 1, wherein
the skin whitening compound or the pharmaceutically acceptable salt of the skin whitening compound has a mass percentage of 0.5% to 30% in an external preparation for skin whitening.

3. The method according to claim 1, wherein
in the step of applying the skin whitening compound or pharmaceutically acceptable salt of the skin whitening compound to skin of the human subject, the skin whitening compound or the pharmaceutically acceptable salt of the skin whitening compound is prepared in the form of an external preparation for skin whitening, wherein the external preparation for skin whitening comprises the skin whitening compound or the pharmaceutically acceptable salt of the skin whitening compound in combination with one or more selected from the group consisting of: an antioxidant, a colorant, a depigmenting agent, an emollient, an emulsifier, an exfoliant, a fragrance, a humectant, a lubricant, a pharmaceutically active agent, a preservative, a skin protectant, a skin penetration enhancer, a sunscreen, a stabilizer, a surfactant, or a thickener.

4. The method according to claim 3, wherein
the skin protectant is toner, lotion, cream, essence, or facial mask.

5. The method according to claim 3, wherein
the external preparation is prepared in a form of an aqueous lotion, a water-in-oil emulsion, an oil-in-water emulsion, an oil lotion, an oleyl alcohol lotion, or a gel.

6. The method according to claim 1, wherein
the skin whitening compound of the formula (I-1) is prepared through the following steps:
step 1: dissolving 3,5-dihydroxyphenylacetic acid and borane-tetrahydrofuran (THF) at a molar ratio of 1:(1.1-1.3) in THF to perform a first reaction at 15° C. to 25° C. for 4 h to 6 h; after the first reaction is completed, conducting a rotary evaporation for removing the THF to obtain a crude product; and purifying the crude product by a column chromatography to obtain an intermediate 2;

step 2: dissolving the intermediate 2 obtained in step 1 and benzyl chloride in acetone by stirring, wherein a molar ratio of the intermediate 2 to the benzyl chloride is 1:(1-1.2); after the dissolution is completed, adding potassium carbonate and potassium iodide to react at reflux for 18 h to 20 h, wherein a molar ratio of the intermediate 2 to the potassium carbonate is 1:(1-1.2) and a molar ratio of the intermediate 2 to the potassium iodide is 1:(0.1-0.2); evaporating the acetone, pouring a residue into water, and adding hydrochloric acid dropwise to adjust a pH to 7; conducting an extraction with ethyl acetate, evaporating the ethyl acetate out from a resulting organic phase under vacuum, and subjecting a resulting product to recrystallization with absolute ethanol to obtain a white solid intermediate 3;

step 3: dissolving the white solid intermediate 3 obtained in step 2 in dichloromethane (DCM), and adding an intermediate 4, a molecular sieve, and dry silver carbonate sequentially under stirring to perform a second reaction at 15° C. to 25° C. for 24 h to 36 h in the dark, wherein a molar ratio of the white solid intermediate 3 to the intermediate 4 is 1:(1.2-1.4), the molecular sieve is added at an amount of 2 g to 3 g, and a molar ratio of the white solid intermediate 3 to the dry silver carbonate is 1:(0.6-0.7); after the second reaction is completed, filtering a first resulting mixture to obtain a filter cake and a first filtrate; and washing the filter cake with DCM, and concentrating the first filtrate to obtain an intermediate 5;

5 step 4: dissolving the intermediate 5 obtained in step 3 in absolute methanol, adding sodium methoxide, and stirring at 15° C. to 25° C. for 6 h to 8 h; adjusting a pH to 6 with acetic acid, filtering a second resulting mixture to obtain a second filtrate, and concentrating the second filtrate under vacuum to obtain a viscous material; adding methanol and palladium carbon to the viscous material, and stirring to react for 4 h to 6 h under a hydrogen pressurization; and purifying a reaction product by the column chromatography to obtain a final product with a structure shown in the formula (I-1):

6

7. The method according to claim 1, wherein inhibiting melanocyte production of melanin results in about a 50% reduction in melanin production.

* * * * *